United States Patent
Lee et al.

(10) Patent No.: US 10,553,730 B2
(45) Date of Patent: Feb. 4, 2020

(54) BROADBAND MULTI-PURPOSE OPTICAL DEVICE AND METHODS OF MANUFACTURING AND OPERATING THE SAME

(71) Applicant: Samsung Electronics Co., Ltd., Suwon-si, Gyeonggi-do (KR)

(72) Inventors: Kiyoung Lee, Seoul (KR); Jinseong Heo, Seoul (KR); Jaeho Lee, Seoul (KR); Haeryong Kim, Seongnam-si (KR); Seongjun Park, Seoul (KR); Hyeonjin Shin, Suwon-si (KR); Eunkyu Lee, Yongin-si (KR); Sanghyun Jo, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/603,796

(22) Filed: May 24, 2017

(65) Prior Publication Data
US 2018/0145190 A1   May 24, 2018

(30) Foreign Application Priority Data
Nov. 21, 2016   (KR) .................. 10-2016-0154881

(51) Int. Cl.
*H01L 31/0216*   (2014.01)
*G01N 21/59*   (2006.01)
(Continued)

(52) U.S. Cl.
CPC ....... *H01L 31/02161* (2013.01); *G01N 21/59* (2013.01); *H01L 31/028* (2013.01);
(Continued)

(58) Field of Classification Search
CPC .......... H01L 31/02161; H01L 31/1804; H01L 31/022466; H01L 31/028; H01L 31/035218; G01N 21/59
See application file for complete search history.

(56) References Cited

U.S. PATENT DOCUMENTS

| | | | | |
|---|---|---|---|---|
| 4,721,983 A * | 1/1988 | Frazier | .................. | B82Y 10/00 257/24 |
| 6,621,145 B2 * | 9/2003 | Murota | ............. | H01L 21/02381 257/607 |

(Continued)

FOREIGN PATENT DOCUMENTS

| | | | | |
|---|---|---|---|---|
| KR | 101471893 B1 * | 12/2014 | ............. | H01L 33/36 |
| KR | 101558801 B1 | 10/2015 | | |
| KR | 1020160049760 A | 5/2016 | | |

OTHER PUBLICATIONS https://www.thefreedictionary.com/pinning.*
(Continued)

*Primary Examiner* — Mohamed K Amara
(74) *Attorney, Agent, or Firm* — Harness, Dickey and Pierce, P.L.C.

(57) ABSTRACT

A broadband multi-purpose optical device includes a semiconductor layer having a light absorption characteristic, a first active layer having a light absorption band different from a light absorption band of the semiconductor layer, a first two-dimensional (2D) material layer adjacent to the first active layer, and a first interfacial layer configured to control a pinning potential of the semiconductor layer and the first active layer. The broadband multi-purpose optical device may further include at least one second active layer, and may include a tandem structure that further includes at least one second 2D material layer. The first active layer and the second active layer may have different light absorption bands. The broadband multi-purpose optical device may (Continued)

further include a second interfacial layer adjacent to the first 2D material layer.

14 Claims, 10 Drawing Sheets

(51) Int. Cl.
*H01L 31/0224* (2006.01)
*H01L 31/028* (2006.01)
*H01L 31/0352* (2006.01)
*H01L 31/18* (2006.01)

(52) U.S. Cl.
CPC ............... *H01L 31/022466* (2013.01); *H01L 31/035218* (2013.01); *H01L 31/1804* (2013.01)

(56) References Cited

U.S. PATENT DOCUMENTS

| | | | | |
|---|---|---|---|---|
| 7,327,000 | B2* | 2/2008 | DeHeer | H01L 21/0405 257/234 |
| 8,178,862 | B2* | 5/2012 | Colinge | B82Y 10/00 257/402 |
| 8,742,398 | B2* | 6/2014 | Klem | B82Y 10/00 257/21 |
| 9,105,556 | B2* | 8/2015 | Heo | H01L 29/7391 |
| 9,478,702 | B2* | 10/2016 | Hwang | F21K 9/232 |
| 9,647,012 | B1* | 5/2017 | Liang | H01L 27/127 |
| 2009/0242871 | A1* | 10/2009 | Kobayashi | C09K 11/025 257/13 |
| 2010/0193025 | A1* | 8/2010 | Serban | B82Y 30/00 136/256 |
| 2010/0258787 | A1* | 10/2010 | Chae | H01L 29/0673 257/39 |
| 2011/0089403 | A1* | 4/2011 | Woo | B82Y 10/00 257/29 |
| 2011/0220865 | A1* | 9/2011 | Miyata | B82Y 10/00 257/12 |
| 2012/0032227 | A1* | 2/2012 | Seabaugh | H01L 29/7391 257/105 |
| 2012/0104432 | A1* | 5/2012 | Shim | H01L 33/42 257/94 |
| 2012/0247543 | A1* | 10/2012 | Zehavi | H01L 31/0747 136/255 |
| 2013/0048951 | A1* | 2/2013 | Heo | B82Y 10/00 257/29 |
| 2013/0285013 | A1* | 10/2013 | An | H01L 21/0237 257/13 |
| 2014/0022025 | A1* | 1/2014 | Jenkins | H03B 7/06 331/116 FE |
| 2014/0158989 | A1* | 6/2014 | Byun | H01L 29/452 257/29 |
| 2014/0231752 | A1* | 8/2014 | Shin | H01L 29/1606 257/29 |
| 2014/0239310 | A1* | 8/2014 | Rho | H01L 21/02425 257/76 |
| 2014/0299838 | A1* | 10/2014 | Lee | H01L 29/66431 257/27 |
| 2015/0194789 | A1* | 7/2015 | Graham | H01S 5/183 372/38.05 |
| 2015/0333196 | A1 | 11/2015 | Shin et al. | |
| 2016/0247841 | A1* | 8/2016 | Cheng | H01L 31/036 |
| 2016/0343891 | A1* | 11/2016 | Heo | H01L 31/035218 |
| 2016/0359062 | A1 | 12/2016 | Heo et al. | |
| 2017/0005207 | A1* | 1/2017 | Li | H01L 31/02327 |
| 2017/0077226 | A1* | 3/2017 | Oh | H01L 21/02425 |
| 2017/0110616 | A1* | 4/2017 | Dissanayake | H01L 31/02167 |
| 2017/0222097 | A1* | 8/2017 | Lub | C09K 11/025 |
| 2017/0236968 | A1 | 8/2017 | Heo et al. | |
| 2017/0250304 | A1 | 8/2017 | Choi et al. | |
| 2018/0175217 | A1* | 6/2018 | White | H01L 31/028 |
| 2018/0204908 | A1* | 7/2018 | Sato | H01L 21/02581 |

OTHER PUBLICATIONS

Mueller, Thomas et al., "Graphene photodetectors for high-speed optical communications", Nature Photonics, vol. 4, pp. 297-300, May 2010, www.nature.com/naturephotonics.
Silvia Masala et al. "The Silicon:Colloidal Quantum Dot Heterojunction", Advanced Materials, 2015 Wiley-VCH Verlag GmbH Co. KGaA, Weinheim, DOI: 10.1002/adma.201503212, www.MaterialsViews.com .
Xi Xiao et al., "Toward high-speed, low-cost, on-chip silicon optical interconnects", SPIE Newsroom, 2010, 10.1117/2.1201012.003309.

* cited by examiner

BROADBAND MULTI-PURPOSE OPTICAL DEVICE AND METHODS OF MANUFACTURING AND OPERATING THE SAME

CROSS-REFERENCE TO RELATED APPLICATION

This application claims the benefit of Korean Patent Application No. 10-2016-0154881, filed on Nov. 21, 2016, in the Korean Intellectual Property Office, the disclosure of which is incorporated herein in its entirety by reference.

BACKGROUND

1. Field

Example embodiments relate to optical devices, and more particularly, to broadband multi-purpose optical devices and methods of manufacturing and operating the broadband multi-purpose optical devices.

2. Description of the Related Art

A Si complementary metal-oxide-semiconductor (CMOS) used in image sensors is a general device manufactured in a silicon process. The Si CMOS is manufactured in the same way as a logic circuit thereunder. Therefore, the Si CMOS may have relatively high process stability and reliability and recent process techniques may be readily applied to manufacture the Si CMOS. Also, the Si CMOS is used in various fields, for example, mobile devices, surveillance devices, or automobiles, because the Si CMOS may be readily miniaturized and is suitable to be used for detection at relatively high speed.

A Si CMOS may be applied to a field that uses a visible light region, and furthermore, its application may be considered in fields using an infrared ray region, in particular, bio-health fields or security fields.

In this way, although the wavelength region band of interest is widened to a broadband region, a Si based image sensor of the related art may not provide a sufficient figure of merits (for example, in terms of responsivity, external quantum efficiency (EQE), detectivity, response time, etc.).

SUMMARY

Example embodiments provide broadband multi-purpose optical devices configured to tune an operation voltage according to optical characteristics to be measured in a broadband region.

Example embodiments also provide methods of manufacturing a broadband multi-purpose optical device.

Example embodiments also provide methods of operating the broadband multi-purpose optical device.

Additional aspects will be set forth in part in the description which follows and, in part, will be apparent from the description, or may be learned by practice of example embodiments.

According to example embodiments, a broadband multi-purpose optical device includes a semiconductor layer having a light absorption characteristic, a first active layer having a light absorption band different from a light absorption band of the semiconductor layer, a two-dimensional (2D) material layer adjacent to the first active layer, and a first interfacial layer configured to control a pinning potential of the semiconductor layer and the first active layer.

The broadband multi-purpose optical device may further include at least one second active layer adjacent to the first 2D material layer. Also, the broadband multi-purpose optical device may have a tandem structure further including at least one second 2D material layer.

The first active layer and the second active layer may have different light absorption bands.

The broadband multi-purpose optical device may further include a second interfacial layer adjacent to the first 2D material layer.

The first interfacial layer may be between the semiconductor layer and the first active layer.

The first interfacial layer may be between the first active layer and the first 2D material layer.

The broadband multi-purpose optical device may further include an electrode on a lower surface of the semiconductor layer.

According to example embodiments, the broadband multi-purpose optical device may further include a base substrate, wherein the first active layer, the first interfacial layer, the semiconductor layer, and the two-dimensional material layer may be sequentially stacked on the base substrate in the stated order from the base substrate.

The first interfacial layer may be one of an oxide material layer, a nitride material layer, a 2D semiconductor, and a non-conductive layer.

The first active layer may be one of a quantum dot layer including a plurality of quantum dots, a 2D material layer, and a thin film semiconductor layer.

Each of the quantum dots may be coated with a chemical ligand when the first active layer is the quantum dot layer including the plurality of quantum dots.

The first interfacial layer may be between the semiconductor layer and the first active layer, and the second interfacial layer may be between the first active layer and the first two-dimensional material layer.

According to example embodiments, a method of manufacturing a broadband multi-purpose optical device includes forming a first interfacial layer on a semiconductor layer having a light absorption characteristic, forming a first active layer on the first interfacial layer, the first active layer being an optical active layer, and forming a first two-dimensional (2D) material layer on the first active layer.

Forming the first interfacial layer may include chemically processing an upper surface of the semiconductor layer to inhibit or prevent the formation of a natural oxide film, and forming the first interfacial layer on the chemically processed upper surface of the semiconductor layer.

The method may further include forming a second interfacial layer on the first 2D material layer before forming the first active layer.

The method may further include forming a second active layer on the first 2D material layer before forming the first active layer.

The method may further include repeatedly and alternately stacking the second active layer and a second two-dimensional (2D) material layer on the first 2D material layer.

According to example embodiments, a method of manufacturing a broadband multi-purpose optical device includes forming an optical active layer on a base substrate, forming an interfacial layer on the optical active layer, forming a thin film semiconductor layer on the interfacial layer, and forming a two-dimensional material layer on the thin film semiconductor layer.

According to example embodiments, a method of operating a broadband multi-purpose optical device includes measuring a first optical characteristic according to light absorption by applying a forwarding bias, and measuring a second optical characteristic according to light absorption by applying a reverse bias after measuring the first optical characteristic, wherein the first and second optical characteristics are measured using a single optical device.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
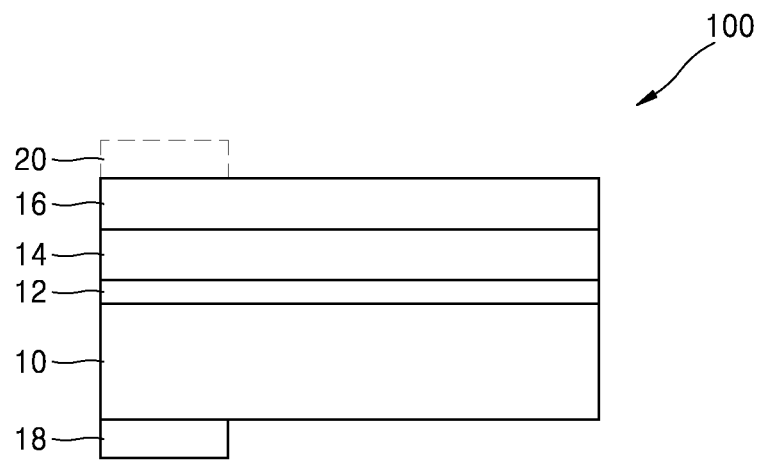
FIG. 1 is a cross-sectional view of a broadband multi-purpose optical device according to example embodiments.

The inventive concepts now will be described more fully hereinafter with reference to the accompanying drawings, in which various embodiments are shown. The inventive concepts may, however, be embodied in many different forms, and should not be construed as limited to the embodiments set forth herein. Rather, these embodiments are provided so that this disclosure will be thorough and complete, and will fully convey the scope of the inventive concepts to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the context clearly indicates otherwise. "At least one" is not to be construed as limiting to "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Broadband multi-purpose optical devices according to example embodiments and methods of manufacturing and operating the broadband multi-purpose optical devices will be described with reference to the accompanying drawings. In the drawings, thicknesses of layers and regions may be exaggerated for clarification of the specification.

FIG. 1 shows a broadband multi-purpose optical device 100 according to example embodiments.

The broadband multi-purpose optical device 100 of FIG. 1 may be an optical detector as a light receiving device.

Referring to FIG. 1, the optical device 100 includes a semiconductor layer 10, an interfacial layer 12, an optical active layer 14, and a two-dimensional 2D (i.e., graphene) layer 16 that are sequentially stacked in the stated order. A lower electrode 18 is disposed on a lower surface of the semiconductor layer 10. The 2D material (i.e., graphene) layer 16 may be used as an upper electrode. The interfacial layer 12 is arranged between the semiconductor layer 10 and the optical active layer 14. The semiconductor layer 10 may be an optical active layer that absorbs light in a specific band. The semiconductor layer 10 may be a semiconductor layer that causes a photoelectric action by absorbing light of visible light region.

The semiconductor layer 10 may be, for example, a silicon substrate. The semiconductor layer 10 may be doped with an n-type dopant or a p-type dopant. The semiconductor layer 10 may have a thickness in a range from about 1 nm to about a few hundreds of μm. The interfacial layer 12 may be used in energy band engineering. Accordingly, the interfacial layer 12 may be referred to as an energy band engineering layer. Due to the action of the interfacial layer 12, a pinning potential between the semiconductor layer 10 and the optical active layer 14 may be controlled, and accordingly, an energy band between the semiconductor layer 10 and the optical active layer 14 may be controlled. That is, a built-in potential between the semiconductor layer 10 and the optical active layer 14 may be controlled. Accordingly, optical characteristics described below will be generated.

The interfacial layer 12 may be an oxide material layer or a nitride material layer. The interfacial layer 12 may be other material layer, for example, a two-dimensional (2D) semiconductor layer or a non-conductive material layer. The interfacial layer 12 may have a thickness of a few nm, for example, in a range from 1 nm to 2 nm. The semiconductor layer 10 may include other semiconductor materials or compound semiconductors besides silicon Si. For example, the semiconductor layer 10 may be a layer formed of Ge or a compound semiconductor of Group III-V material. A surface of the semiconductor layer 10 on which the interfacial layer 12 is formed may be a chemically processed surface. For example, an upper surface of the semiconductor layer 10 may be a $H_2$-terminated surface.

The optical active layer 14 may be a transparent material layer with respect to light. The optical active layer 14 may have a small thickness so carriers excited by a photoelectric action may tunnel therethrough when a voltage is applied to the optical active layer 14. For example, the optical active layer 14 may have a thickness in a range from about 1 nm to about a few hundreds of μm. The optical active layer 14 may be a quantum dot layer including a plurality of quantum dots or a 2D Van der Waals (vdW) layer. The quantum dot layer may be a colloidal quantum dot (CQD) layer, for example, a PdS CQD layer or an $Ag_2S$ CQD layer. When the optical active layer 14 is a quantum dot layer, the optical active layer 14 may be a layer coated on the upper surface of the semiconductor layer 10.

When the optical active layer 14 is a quantum dot layer, each surface of the quantum dots included in the quantum dot layer may be chemically processed to protect the quantum dots. For example, each of the quantum dots included in the quantum dot layer may be coated with a chemical ligand. According to the thickness of the optical active layer 14, a resistance between the optical active layer 14 and the semiconductor layer 10 may be controlled. When the optical active layer 14 is a quantum dot layer, a resistance between the optical active layer 14 and the semiconductor layer 10 may vary according to the type of the chemical ligand coated on surfaces of the quantum dots included in the quantum dot layer. The optical active layer 14 may be a 2D material layer (hereinafter, a 2D semiconductor material) that shows a semiconductor characteristics. The 2D semiconductor material may be, for example, $MoS_2$, $WSe_2$, etc. The optical active layer 14 may be a thin semiconductor. The optical active layer 14 may be doped with an n-type dopant or a p-type dopant.

The optical active layer 14 may have an optical characteristic showing maximum absorption efficiency at a given specific wavelength. When the optical active layer 14 is a quantum dot layer including CQDs, due to the characteristic of CQDs, a significant amount of light absorption may occur in other short wavelength regions. Thus, the broadband multi-purpose optical device according to example embodiments may have higher optical characteristics when compared to a light receiving device that does not include the optical active layer 14, that is, a light receiving device having the semiconductor layer 10 as the main active layer. Also, due to the presence of the optical active layer 14, the broadband multi-purpose optical device has a relatively high optical absorption characteristic in a near infrared ray region-infrared ray region, and thus, may have a relatively high light receiving effect in various wavelength regions besides the visible light region.

The 2D material (i.e., graphene) layer 16 may be used as one of the transparent electrodes. The 2D material (i.e., graphene) layer 16 may be used as an upper electrode that does not show an energy pinning effect. Although the 2D material (i.e., graphene) layer 16 may be used as an upper electrode, an upper electrode 20 may be additionally arranged on a region of the 2D material (i.e., graphene) layer 16. The 2D material (i.e., graphene) layer 16 may be a protection layer that protects the optical active layer 14. For example, if the optical active layer 14 includes a material that is weak with respect to an external material (for example, an organic material or air), the optical active layer 14 may be protected by covering a whole upper surface of the optical active layer 14 with the 2D material (i.e., graphene) layer 16. The 2D material (i.e., graphene) layer 16 may be doped with an n-type dopant or a p-type dopant. A 2D material layer may be used instead of the 2D material (i.e., graphene) layer 16.

Figure 2:
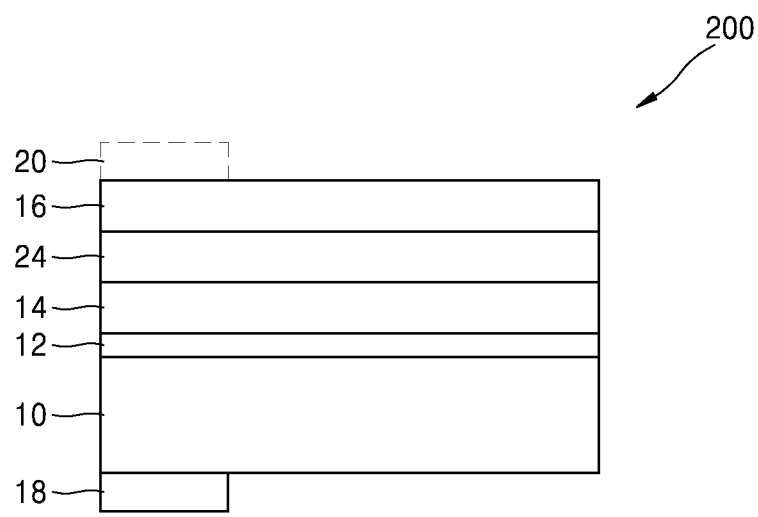
FIG. 2 is a cross-sectional view of a broadband multi-purpose optical device according to example embodiments.

FIG. 2 is a cross-sectional view of a broadband multi-purpose optical device 200 according to example embodiments. For the sake of convenience, only parts different from the broadband multi-purpose optical device 100 of FIG. 1 are described.

Referring to FIG. 2, the broadband multi-purpose optical device 200 may further include a second active layer 24 between the 2D material (i.e., graphene) layer 16 and the optical active layer 14. The second active layer 24 may directly contact the 2D material (i.e., graphene) layer 16 and the optical active layer 14. A material layer used as the second active layer 24 may be the same as a material layer used as the optical active layer 14. In a layer structure in which the optical active layer 14 and the second active layer 24 are sequentially arranged, the material layers 14 and 24 may have different band gaps from each other. Accordingly, the center bands of optical absorption of the optical active layer 14 and the second active layer 24 may be different. As a result, the broadband multi-purpose optical device 200 may further largely absorb light of various bands.

The case in which the optical active layer 14 and the second active layer 24 are arranged between the interfacial layer 12 and the 2D material (i.e., graphene) layer 16 has been described, more than three active layers may be arranged between the interfacial layer 12 and the 2D material (i.e., graphene) layer 16.

In this manner, light of a wider band may be distinguished and detected by arranging a plurality of optical active layers between the interfacial layer 12 and the 2D material (i.e., graphene) layer 16.

Figure 3:
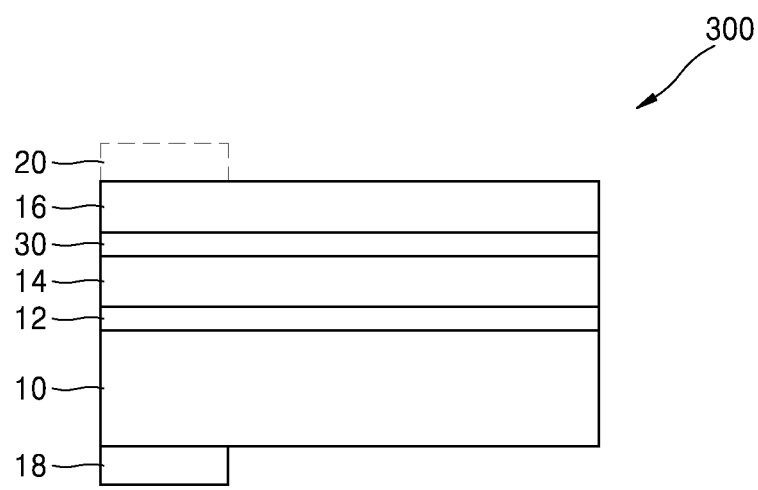
FIGS. 3 through 5 are cross-sectional views of broadband multi-purpose optical devices according to example embodiments.

FIG. 3 is a cross-sectional view of broadband multi-purpose optical device 300 according to example embodiments. Different parts from the broadband multi-purpose optical device 100 of FIG. 1 will be described below.

Referring to FIG. 3, the broadband multi-purpose optical device 300 includes a second interfacial layer 30 between the optical active layer 14 and the 2D material (i.e., graphene) layer 16, and thus, includes two interfacial layers. The second interfacial layer 30 may directly contact the 2D material (i.e., graphene) layer 16 and the optical active layer 14. The second interfacial layer 30 may include the same material layer as the interfacial layer 12. The broadband multi-purpose optical device 300 may include the second interfacial layer 30 of the interfacial layer 12 and the second interfacial layer 30.

Figure 4:
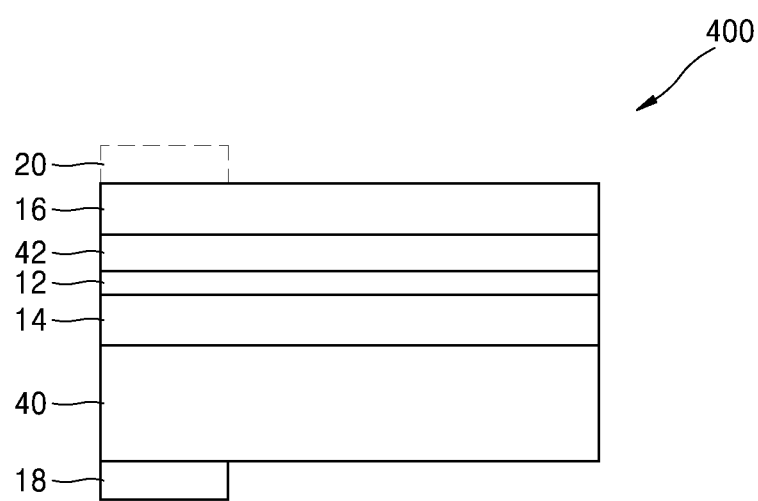

FIG. 4 is a cross-sectional view of broadband multi-purpose optical device 400 according to example embodiments. Like reference numerals are used to indicate like elements of FIG. 1.

Referring to FIG. 4, the optical active layer 14, the interfacial layer 12, a thin film semiconductor layer 42, and the 2D material (i.e., graphene) layer 16 are sequentially stacked on a base substrate 40, and the adjacent material layers may contact each other. The base substrate 40 may be a transparent substrate. The thin film semiconductor layer 42 may have approximately a nanometer level thickness and may be transparent. The thin film semiconductor layer 42 may have a relatively high absorption rate at a visible light region, and may have a relatively low absorption rate at an infrared ray region. The light absorption rate of the optical active layer 14 may be relatively high in an infrared ray region. The thin film semiconductor layer 42 may be, for example, a Si layer doped with an n-type dopant.

Figure 5:
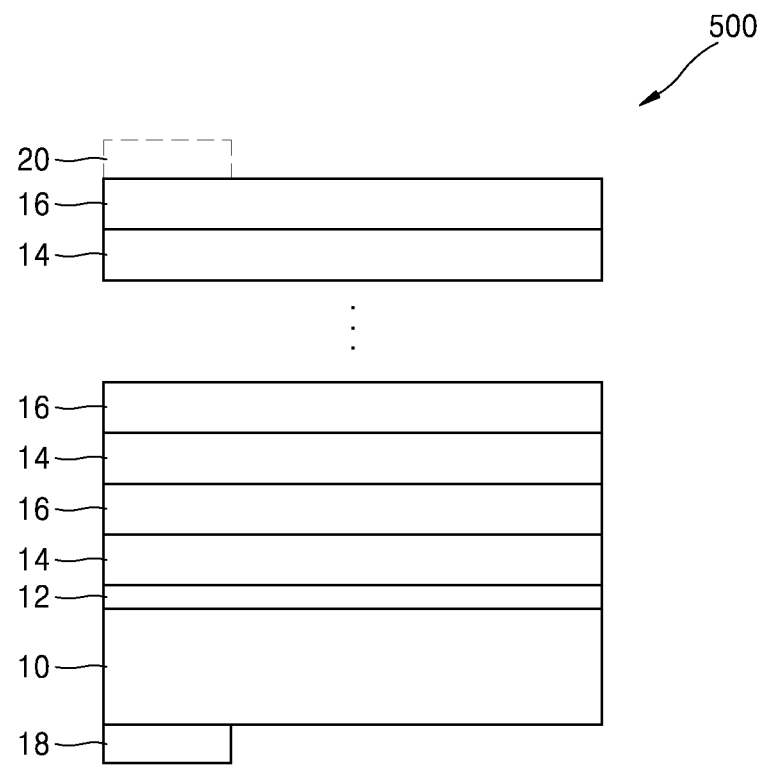

FIG. 5 is a cross-sectional view of broadband multi-purpose optical device 500 according to example embodiments. Like reference numerals are used to indicate like elements of FIG. 1. The broadband multi-purpose optical device 500 may have a tandem structure.

Referring to FIG. 5, the broadband multi-purpose optical device 500 includes a layer structure in which the optical active layer 14 and the 2D material (i.e., graphene) layer 16 are alternately and repeatedly stacked on the interfacial layer 12. The number of alternate stacks of the optical active layer 14 and the 2D material (i.e., graphene) layer 16 may be at least two. In this manner, because the optical active layer 14 and the 2D material (i.e., graphene) layer 16 are alternately stacked, an overall thickness of the optical active layer 14 is increased, and thus, the amount of light absorption is increased and a light absorption band may be increased.

The broadband multi-purpose optical devices 100 through 500 depicted in FIGS. 1 through 5 may be modified into various types through combining each of the devices, modifying constituent elements, or adding other elements between layers. The size of each of the broadband multi-purpose optical devices 100 through 500 of FIGS. 1 through 5 may be in a range from about a few nm to about a few hundreds of μm.

The broadband multi-purpose optical devices 100 through 500 described above show a photoelectric action of an optical device by absorbing light, and thus, may be applied to a solar cell.

Optical characteristics of the broadband multi-purpose optical device 100 according to example embodiments will be described below.

Figure 6A:
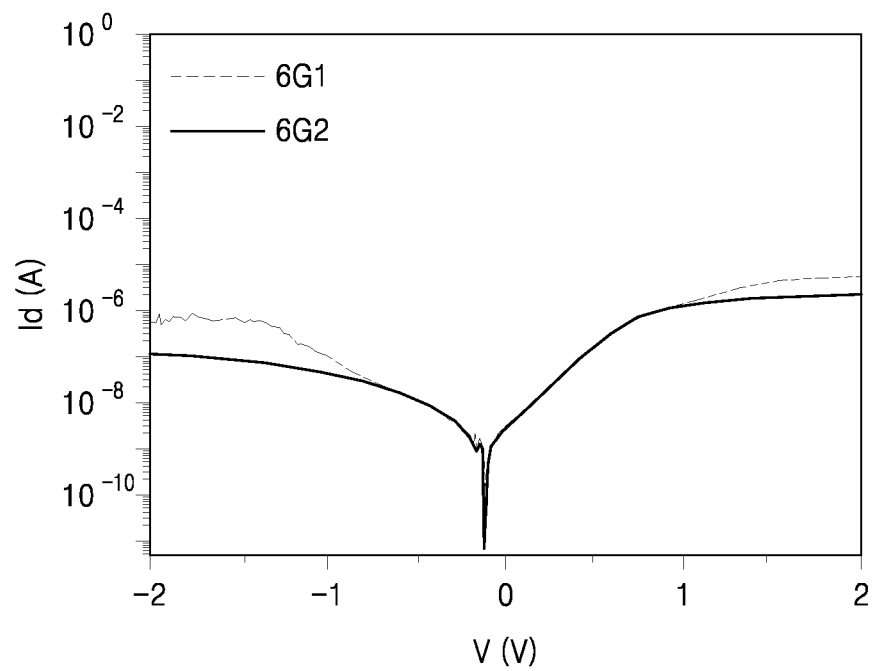
FIGS. 6(a) through 6(b) are graphs showing as a log function current-voltage characteristics of a photoelectric action of an optical device according to example embodiments and a photoelectric action of a related optical device.
Figure 6B:
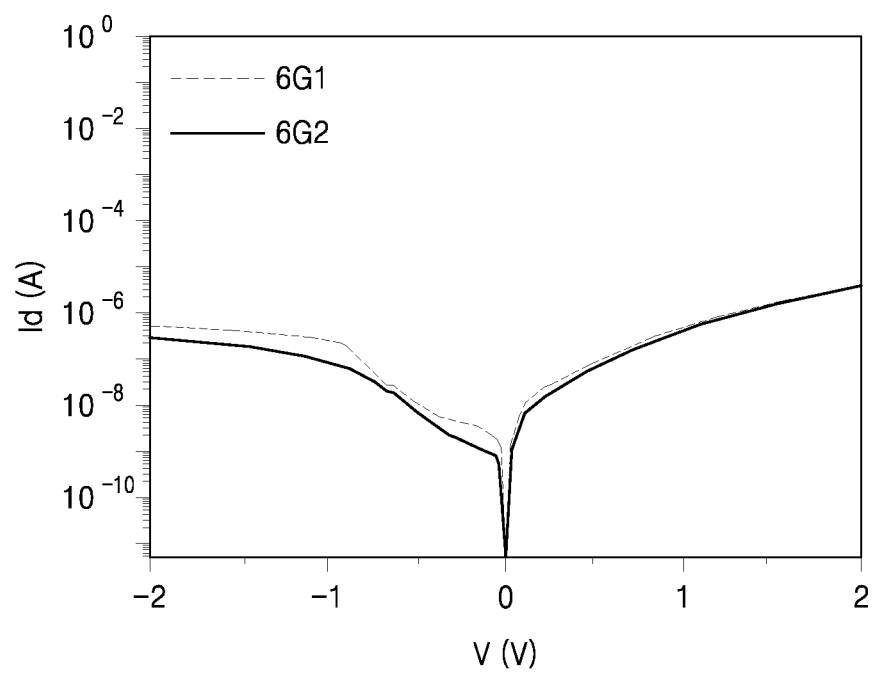

FIGS. 6A-6B are graphs showing a log function of current-voltage characteristics of a photoelectric action of the broadband multi-purpose optical device 100 according to example embodiments and a photoelectric action of an optical device of the related art.

FIG. 6(a) shows a current-voltage characteristic of the broadband multi-purpose optical device 100 according to example embodiments, and FIG. 6(b) shows a current-voltage characteristic of a related art.

The result of FIG. 6(a) was obtained by irradiating light of a wavelength of 850 nm to the broadband multi-purpose optical device 100. At this point, in the broadband multi-purpose optical device 100, an Si layer doped with an n-type dopant as the semiconductor layer 10, an oxide layer (for example, a $SiO_2$ layer) as the interfacial layer 12, a PbS CQD layer as the optical active layer 14, and a graphene sheet as the 2D material (i.e., graphene) layer 16 are used.

The result of FIG. 6(b) was obtained by irradiating light of a wavelength of 850 nm to an optical device of the related art that includes a semiconductor layer (an Si layer doped with an n-type dopant) and a graphene layer (a graphene sheet) that are sequentially stacked.

In FIGS. 6(a)-6(b), a horizontal axis indicates voltage, and a vertical axis indicates current.

In FIGS. 6(a)-6(b), a first graph 6G1 is the current-voltage characteristic with respect to light of a wavelength of 850 nm, and a second graph 6G2 is the current-voltage characteristic when there is no light.

When FIGS. 6(a) and 6(b) are compared, in the case of FIG. 6(a), photoelectric characteristics are showed in both positive voltage region and a negative voltage region, and measured current values when light is irradiated and light is not irradiated are different. However, in the case of FIG. 6(b), a photoelectric characteristic is showed only in the negative voltage region.

From the results of FIGS. 6(a)-6(b), in the case of the broadband multi-purpose optical device 100 according to example embodiments, it is seen that a photoelectric characteristic is generated in both a forward bias region and a reverse bias region, through energy band engineering, by the interfacial layer 12.

Figure 7:
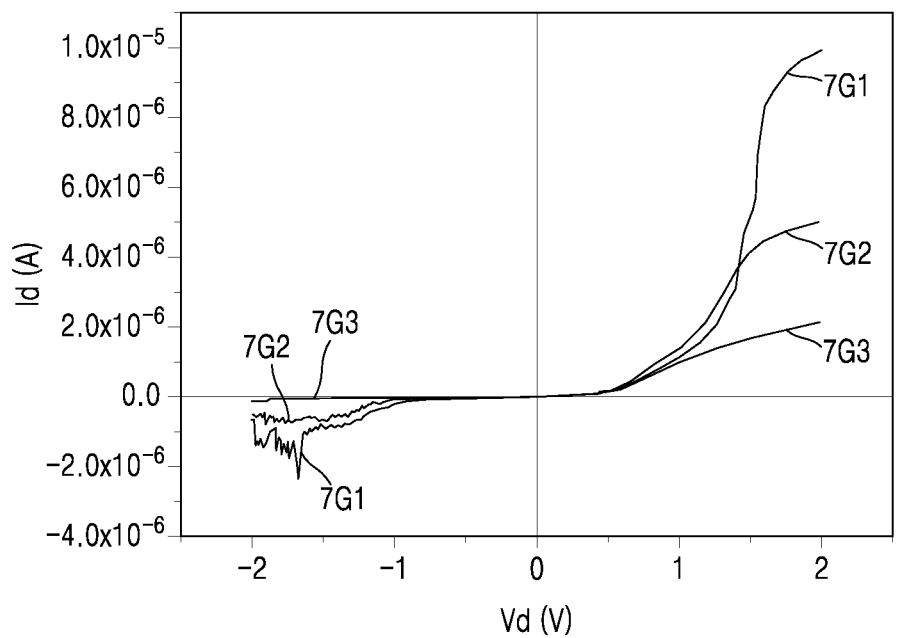
FIG. 7 is a graph showing as a linear function a current-voltage characteristic of a photoelectric action of an optical device according to example embodiments.

FIG. 7 is a graph showing a linear function of current-voltage characteristic of a photoelectric action of the broadband multi-purpose optical device 100 according to example embodiments.

In order to obtain the result of FIG. 7, an optical device used for obtaining the result of FIG. 6(a) was used, and lights having wavelengths 514 nm and 850 nm were irradiated to the optical device.

In FIG. 7, a horizontal axis indicates voltage, and a vertical axis indicates current.

In FIG. 7, a first graph 7G1 is a result when light having a wavelength of 514 nm (visible light region) is irradiated, a second graph 7G2 is a result when light having a wavelength of 850 nm is irradiated, and a third graph 7G3 is a result when no light is irradiated.

Referring to FIG. 7, photoelectric characteristics are shown in both a positive voltage region and a negative voltage region, and in particular, the photoelectric characteristic is large in the positive voltage region.

The result of FIG. 7 may suggest that the broadband multi-purpose optical device 100 according to example embodiments has both relatively high reactivity and external quantum efficiency (EQE) with respect to the visible light region and the infrared ray region in the positive voltage region.

Figure 8A:
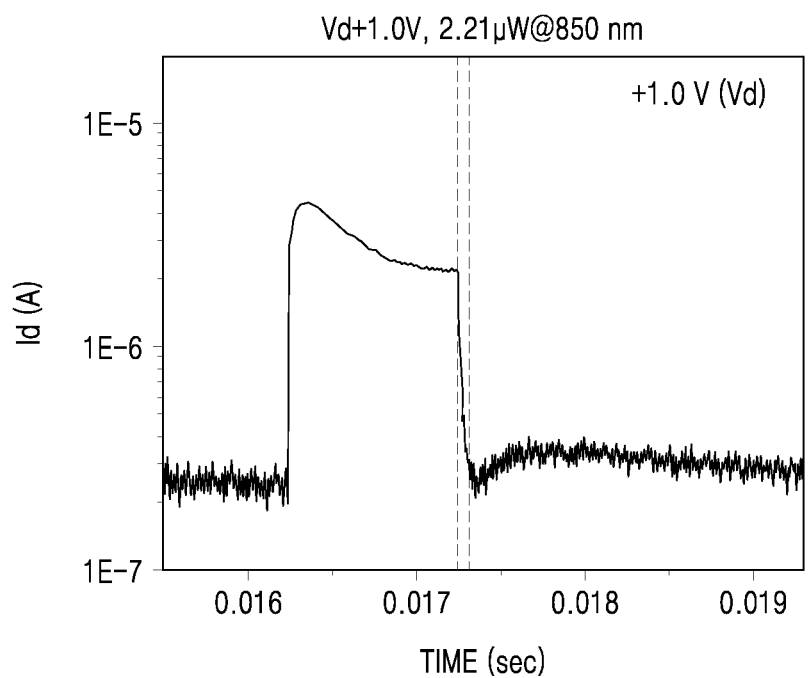
FIGS. 8(a) through 8(c) are graphs showing a measurement result of a photo-transient characteristic that indicates a reaction velocity as one of optical characteristics of an optical device according to example embodiments.
Figure 8B:
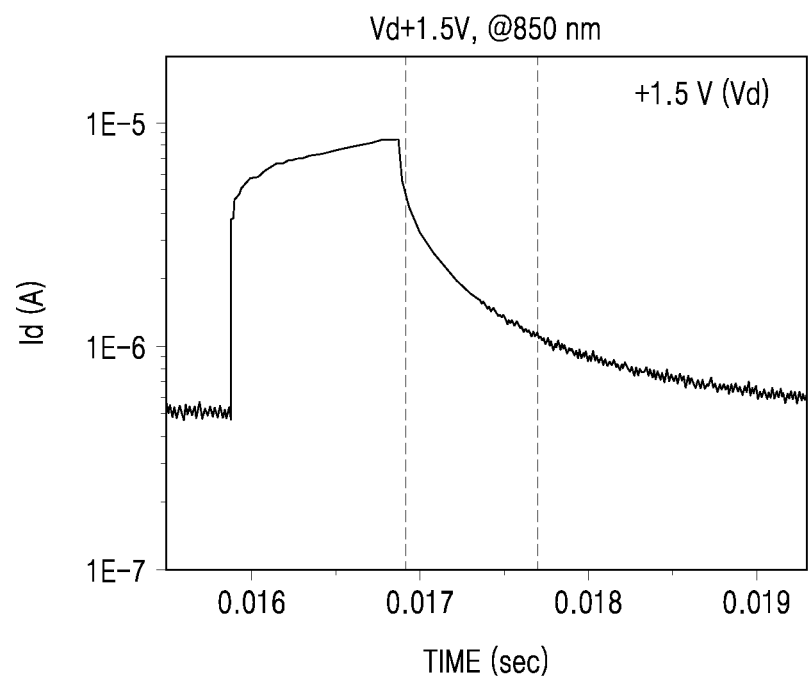
Figure 8C:
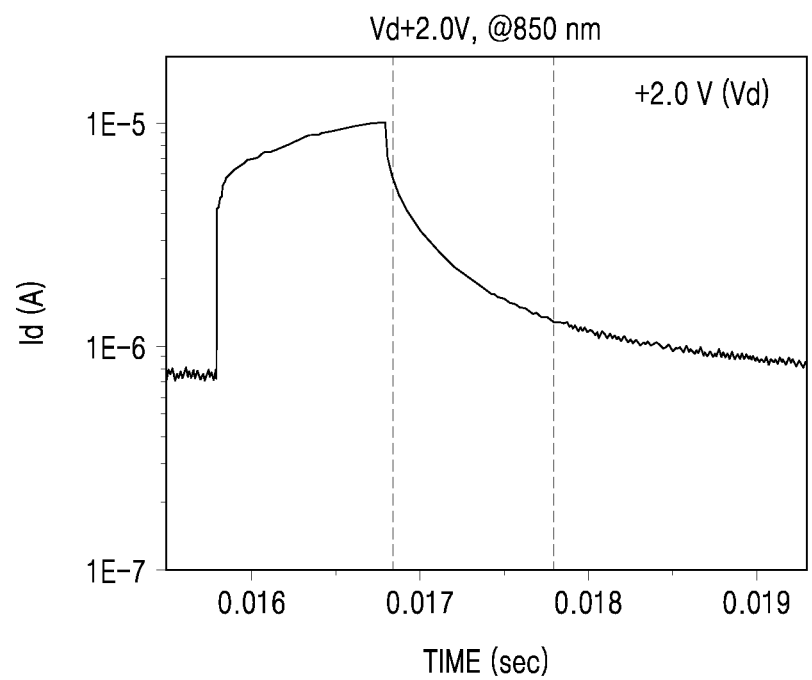

FIGS. 8(a)-8(c) are graphs showing a measurement result of a photo-transient characteristic that indicates a reaction velocity as one of optical characteristics of the broadband multi-purpose optical device 100 according to example embodiments.

The results of FIG. 8(a)-8(c) were obtained by irradiating light of 850 nm to the broadband multi-purpose optical device 100 that was used to obtain the result of FIG. 6(a).

FIG. 8(a) shows a result of photo-transient characteristic obtained by applying +1.0 V as an operation voltage between the lower electrode 18 and the upper electrode (the 2D material (i.e., graphene) layer) 16 while irradiating light to the broadband multi-purpose optical device 100.

FIG. 8(b) shows a result of photo-transient characteristic obtained by applying +1.5 V as an operation voltage between the lower electrode 18 and the upper electrode (the 2D material (i.e., graphene) layer) 16 while irradiating light to the broadband multi-purpose optical device 100.

FIG. 8(c) shows a result of photo-transient characteristic obtained by applying +2.0 V as an operation voltage between the lower electrode 18 and the upper electrode (the 2D material (i.e., graphene) layer) 16 while irradiating light to the broadband multi-purpose optical device 100.

In FIGS. 8(a)-8(c), a horizontal axis indicates time, and a vertical axis indicates current.

When FIGS. 8(a)-8(c) are compared, it is seen that a reaction velocity varies from a few microseconds (μs) to a few seconds according to an applying voltage.

Figure 9:
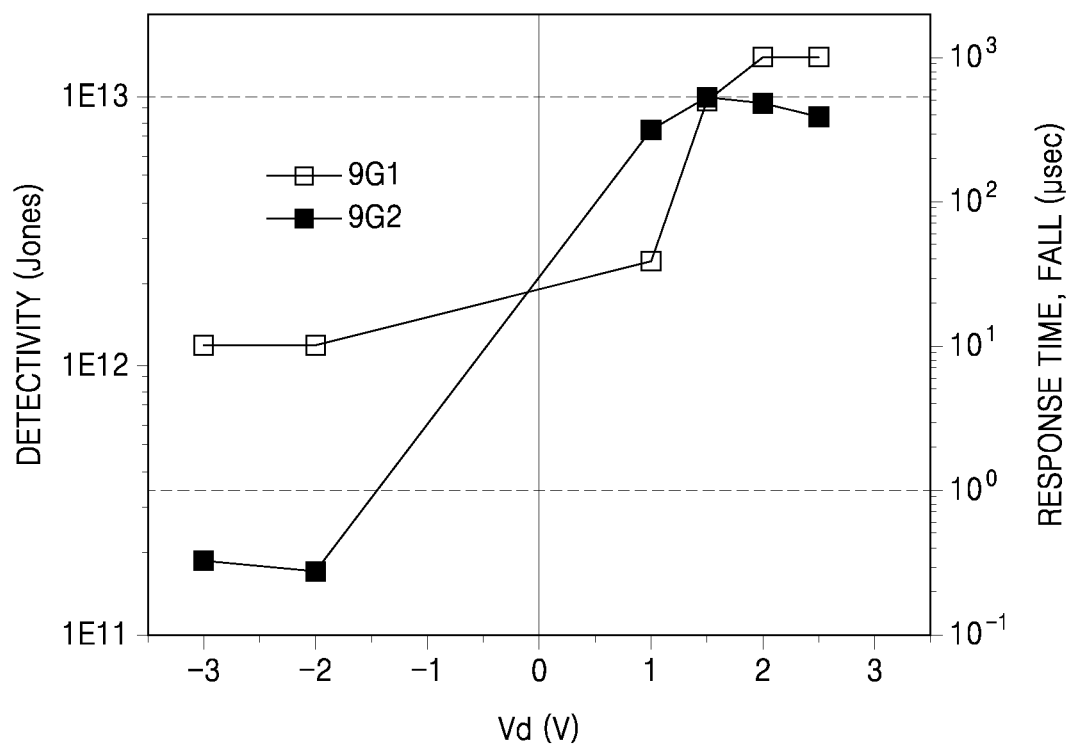
FIG. 9 is a graph showing measurement results of detectivity and reaction time of an optical device according to example embodiments.

FIG. 9 is a graph showing measurement results of detectivity and reaction time of the broadband multi-purpose optical device 100 according to example embodiments.

The result of FIG. 9 was obtained by irradiating light of 850 nm to the broadband multi-purpose optical device 100 that was used to obtain the result of FIG. 6 (a).

In FIG. 9, a horizontal axis indicates voltage, a left vertical axis indicates detectivity, and a right vertical axis indicates reaction time.

In FIG. 9, a first graph 9G1 shows a reaction time according to an applying voltage, and a second graph 9G2 shows detectivity according to an applying voltage.

Referring to graphs 9G1 and 9G2 of FIG. 9, the relationship between the detectivity and the reaction time may be seen. That is, detectivity is relatively high and reaction time is relatively long at a positive region (a forward bias region), and the detectivity is relatively low and reaction time is relatively short at a negative voltage region (a reverse bias region).

Table 1 summarizes values of optical characteristics according to an applying voltage to the broadband multi-purpose optical device 100 according to the example embodiments. The result of Table 1 was obtained using the broadband multi-purpose optical device 100 used to obtain the result of FIG. 6(a).

TABLE 1

| $V_d(V)$ | EQE(R) | D* | $I_{dark}$ (A) | $T_{fall}$ (μs) |
|---|---|---|---|---|
| −3.0 | 18.92(0.13) | $1.85 \times 10^{11}$ | $1.5 \times 10^{-6}$ | ~10 |
| −2.0 | 12.73(0.087) | $1.73 \times 10^{11}$ | $7.8 \times 10^{-7}$ | ~10 |
| +1.0 | 286.6(1.96) | $7.45 \times 10^{12}$ | $2.1 \times 10^{-7}$ | 38 |
| +1.5 | 556.28(3.81) | $9.61 \times 10^{12}$ | $4.9 \times 10^{-7}$ | ~500 |
| +2.0 | 648.69(4.45) | $9.27 \times 10^{12}$ | $7.2 \times 10^{-7}$ | <1,000 |
| +2.5 | 648.49(4.445) | $8.2 \times 10^{12}$ | $1 \times 10^{-6}$ | <1,000 |

Referring to FIG. 9 and Table 1, the sensitivity or detectivity is relatively higher in the forward bias region (the positive voltage region) than in the reverse bias region (the negative voltage region), and the reactivity is relatively higher in the reverse bias region (the negative voltage region) than in the forward bias region (the positive voltage region).

When taking into account the optical characteristics described above, the broadband multi-purpose optical device 100 according to example embodiments may be operated in various ways in matching desired optical characteristics. For example, when relatively high sensitivity and information at a level of stationary image are required, the broadband multi-purpose optical device 100 according to example embodiments may be operated by applying a forward bias. Also, when a relatively rapid reaction velocity is required although the sensitivity is relatively low, the broadband multi-purpose optical device 100 according to example embodiments may be operated by changing the polarity of the applying voltage, that is, by applying a reverse bias.

In this manner, the single broadband multi-purpose optical device 100 according to example embodiments may be used for realizing various optical characteristics.

Figure 10:
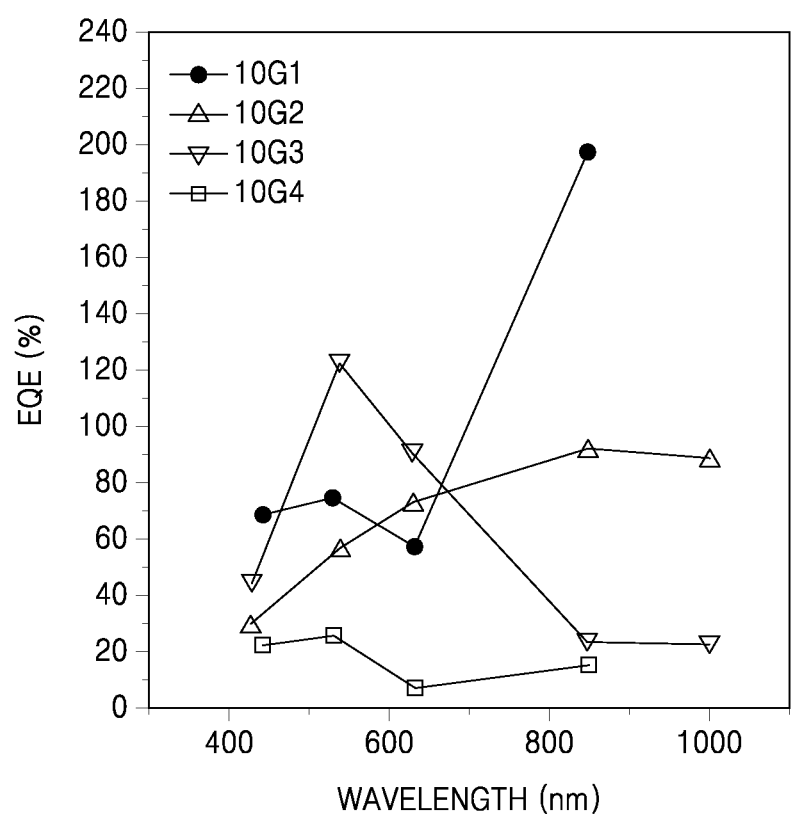
FIG. 10 is a graph showing external quantum efficiencies (EQE) of wavelengths with respect to optical devices according to example embodiments and conventional optical devices.

FIG. 10 is a graph showing external quantum efficiencies (EQE) of wavelengths with respect to optical devices according to example embodiments and conventional optical devices.

In FIG. 10, a first graph 10G1 shows a result of the broadband multi-purpose optical device 100 according to example embodiments. An optical device used to obtain the above result is the same optical device used to obtain the result of FIG. 6(a). However, an SOI layer doped with an n-type dopant is used instead of an n-doping Si layer as the semiconductor layer 10 and an $Ag_2S$ CQD layer is used instead of a PdS CQD layer as the optical active layer 14. Also, an operating voltage of −2.0 V was applied to the optical devices.

In FIG. 10, graphs 10G2 through 10G4 show the EQE results with respect to conventional first through third optical devices. A Si based PN diode was used as the conventional first optical device. An optical device including a Si layer doped with an n-type dopant and a graphene layer that are sequentially stacked was used as the conventional second optical device and a voltage of −1.0 V was applied to the conventional second optical device. An optical device including an SOI layer doped with an n-type dopant and a graphene layer that are sequentially stacked was used as the conventional third optical device, and a voltage of −6.0 V was applied to the conventional third optical device.

In FIG. 10, a horizontal axis indicates wavelength, and a vertical axis indicates EQE.

When the first through fourth graphs 10G1 through 10G4 are compared, in a wide band wavelength region including a visible light region and an infrared ray region, it is seen that the EQE of the broadband multi-purpose optical device 100 according to example embodiments is improved compared to optical devices of the related art. Accordingly, the broadband multi-purpose optical device 100 according to example embodiments may be used as a relatively high sensitivity optical detector in a wideband region.

Methods of manufacturing the broadband multi-purpose optical device 100 according to example embodiments will be described with reference to FIGS. 11 through 13.

Figure 11:
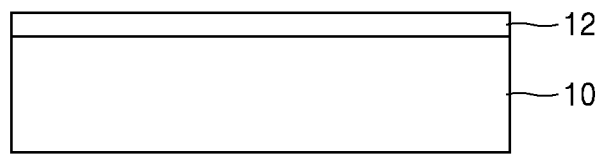
FIGS. 11 through 13 are cross-sectional views illustrating a method of manufacturing a broadband multi-purpose optical device according to example embodiments.

Referring to FIG. 11, the interfacial layer 12 is formed on the semiconductor layer 10. The interfacial layer 12 may cover a whole upper surface of the semiconductor layer 10. The upper surface of the semiconductor layer 10 may be chemically processed before forming the interfacial layer 12 to inhibit or prevent the formation of a natural oxide film thereon. For example, the upper surface of the semiconductor layer 10 may be processed with hydrogen ($H_2$-terminated). The semiconductor layer 10 may include silicon, germanium, or Group III-V chemical compound semiconductor. The semiconductor layer 10 may be doped with an n-type dopant or a p-type dopant in the course of manufacturing or after manufacturing the semiconductor layer 10. The interfacial layer 12 may have a nano level thickness, for example, 10 nm or less, that is, in a range from 1 nm to 2 nm. The interfacial layer 12 may be an oxide film or a nitride film. The interfacial layer 12 may be formed using an atomic layer deposition (ALD) method, but is not limited thereto.

Figure 12:
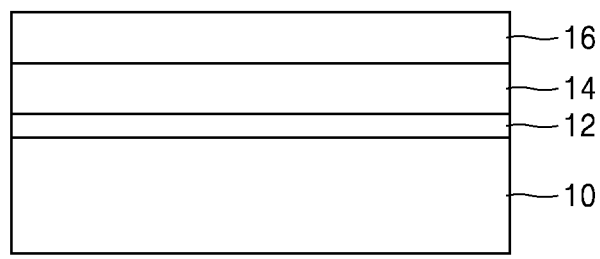

Referring to FIG. 12, the optical active layer 14 is formed on the interfacial layer 12. The optical active layer 14 may be formed as a quantum dot layer including a plurality of quantum dots, a 2D semiconductor material layer, or a thin semiconductor layer. When the optical active layer 14 is a quantum dot layer including a plurality of quantum dots, each of the quantum dots may be coated with a chemical ligand. The 2D material (i.e., graphene) layer 16 is formed on the optical active layer 14. The 2D material (i.e., graphene) layer 16 may be formed in various types. For example, the 2D material (i.e., graphene) layer 16 may be formed as a graphene sheet. The 2D material (i.e., graphene) layer 16 may cover a whole upper surface of the optical active layer 14. The 2D material (i.e., graphene) layer 16 may be directly formed on the optical active layer 14, but may be formed by transferring graphene that is separately formed. The 2D material (i.e., graphene) layer 16 may be used as an upper electrode.

Figure 13:
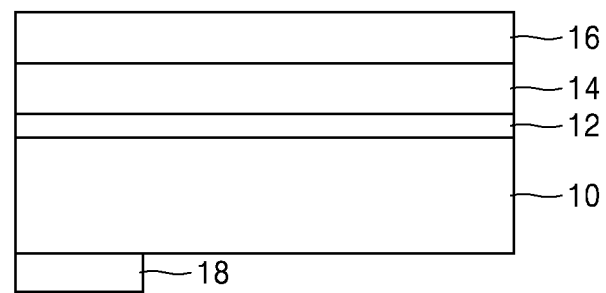

As depicted in FIG. 13, the lower electrode 18 is formed on a lower surface of the semiconductor layer 10. The lower electrode 18 may be, for example, a metal electrode. The lower electrode 18 may be formed by attaching a metal layer to the lower surface of the semiconductor layer 10 or patterning the metal layer.

As described above with reference to FIG. 1, the upper electrode 20 may further be additionally formed on the 2D material (i.e., graphene) layer 16.

In the method of manufacturing the broadband multi-purpose optical device 100, the interfacial layer 12 or the optical active layer 14 may be added as depicted in FIGS. 2 and 3. Also, as depicted in FIG. 4, the broadband multi-purpose optical device 100 may be formed by sequentially stacking the optical active layer 14, the thin Si layer, and the 2D material (i.e., graphene) layer 16 on the base substrate 40 after preparing the base substrate 40. Also, as depicted in FIG. 5, the broadband multi-purpose optical device 100 may be formed by alternately and repeatedly stacking the optical active layer 14 and the 2D material (i.e., graphene) layer 16.

A method of operating the broadband multi-purpose optical device according to example embodiments will be described.

Figure 14:
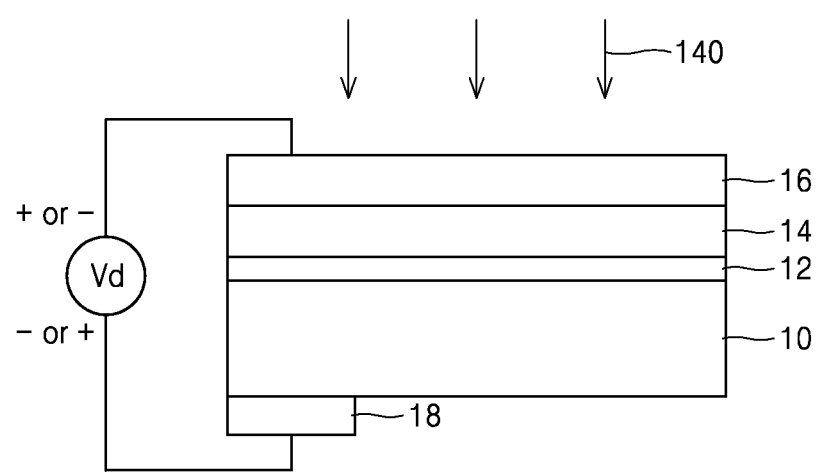
FIG. 14 is a cross-sectional view for explaining a method of operating a broadband multi-purpose optical device according to example embodiments.

As depicted in FIG. 14, an operating voltage Vd is applied between the 2D material (i.e., graphene) layer 16 and the lower electrode 18. In this state, light 140 is irradiated onto the broadband multi-purpose optical device 100, and a current generated by a photoelectric action is measured.

As described with reference to FIGS. 6 and 7, in the case of the broadband multi-purpose optical device 100 according to example embodiments, a photoelectric characteristic is generated in both the positive voltage region (the forward bias region) and the negative voltage region (the reverse bias region). Also, as it may be seen from FIG. 9 and Table 1, a voltage region measured as being relatively high varies according to the photoelectric characteristic, and thus, in the operation process, the polarity of a voltage applied to the broadband multi-purpose optical device 100 may be changed according to an optical characteristic to be measured.

For example, when a relatively high sensitivity and information of a level of a stationary image are required, as shown in Table 1, a small positive voltage greater than 0V and less than 3V (a forward bias) may be applied. Also, when a relatively short response time is required although the sensitivity is relatively low, the polarity of the voltage may be changed, that is, a negative voltage (a reverse bias) may be applied to the broadband multi-purpose optical device 100.

In the operating method described above, the voltage application may be sequentially controlled. For example, after measuring a first optical characteristic (for example, sensitivity) as a main characteristic, a reaction velocity may be consecutively measured as the main characteristic.

In the broadband multi-purpose optical device according to example embodiments described above, an interfacial layer having a relatively small thickness is present between the semiconductor layer and an optical active layer. With the aids of the interfacial layer, a pinning potential between the two layers is controlled, and thus, a built-in potential between the two layers may be controlled. Accordingly, a photoelectric characteristic may be generated in both a positive voltage region (a forward bias region) and a negative voltage region (a reverse bias region). Accordingly, when the broadband multi-purpose optical device according to example embodiments is used, characteristics related to light detection may be measured in both bias regions.

The characteristics related to light detection may be desirable or undesirable in the positive voltage region and the negative voltage region. Therefore, optical characteristics may be measured by changing the polarity of a voltage (an operation voltage) being applied to the broadband multi-purpose optical device according to the optical characteristics to be measured. That is, the broadband multi-purpose optical device according to example embodiments, as a single device, may measure various optical characteristics by controlling the operation voltage.

Also, the broadband multi-purpose optical device according to example embodiments uses a quantum dot layer or a 2D semiconductor layer together with a Si semiconductor layer as an optical active layer, and thus, may measure optical characteristics in a wideband region including a visible light region and an infrared ray region.

While one or more example embodiments have been described with reference to the figures, it will be understood by those of ordinary skill in the art that various changes in form and details may be made therein without departing from the spirit and scope as defined by the following claims.

What is claimed is:

1. A broadband multi-purpose optical device comprising:
    a semiconductor layer having a light absorption characteristic;
    a first active layer having a light absorption band different from a light absorption band of the semiconductor layer;
    a first two-dimensional (2D) material layer on an upper surface of the first active layer such that the first 2D material layer is adjacent to the first active layer; and
    a first interfacial layer in contact with the first active layer and separated from the first 2D material layer, the first interfacial layer configured to control a pinning potential of the semiconductor layer and the first active layer,
    wherein
        all of the first active layer, the first 2D material layer and the first interfacial layer are stacked on one surface of the semiconductor layer in a direction perpendicular to the one surface of the semiconductor layer.

2. The broadband multi-purpose optical device of claim 1, further comprising:
    at least one second active layer adjacent to the first 2D material layer.

3. The broadband multi-purpose optical device of claim 2, wherein the broadband multi-purpose optical device comprises a tandem structure further including at least one second 2D material layer.

4. The broadband multi-purpose optical device of claim 2, wherein the first active layer and the second active layer have different light absorption bands.

5. The broadband multi-purpose optical device of claim 1, further comprising:
    a second interfacial layer adjacent to the first 2D material layer.

6. The broadband multi-purpose optical device of claim 5, wherein
    the first interfacial layer is between the semiconductor layer and the first active layer; and
    the second interfacial layer is between the first active layer and the first 2D material layer.

7. The broadband multi-purpose optical device of claim 1, wherein the first interfacial layer is between the semiconductor layer and the first active layer.

8. The broadband multi-purpose optical device of claim 1, wherein the first interfacial layer is between the first active layer and the first 2D material layer.

9. The broadband multi-purpose optical device of claim 1, further comprising:
    an electrode on a lower surface of the semiconductor layer.

10. The broadband multi-purpose optical device of claim 1, further comprising:
    a base substrate, wherein the first active layer, the first interfacial layer, the semiconductor layer, and the 2D material layer are sequentially stacked on the base substrate.

11. The broadband multi-purpose optical device of claim 1, wherein the first interfacial layer is one of an oxide material layer, a nitride material layer, a 2D semiconductor layer, and a non-conductive layer.

12. The broadband multi-purpose optical device of claim 1, wherein the first active layer is one of a quantum dot layer including a plurality of quantum dots, a 2D semiconductor material layer, and a thin film semiconductor layer.

13. The broadband multi-purpose optical device of claim 12, wherein the first active layer is the quantum dot layer and each of the plurality of quantum dots is coated with a chemical ligand.

14. A method of operating the broadband multi-purpose optical device of claim 1, the method comprising:
    measuring a first optical characteristic according to light absorption by applying a forwarding bias; and
    measuring a second optical characteristic according to light absorption by applying a reverse bias after measuring the first optical characteristic,
    wherein the first and second optical characteristics are measured using a single optical device.

* * * * *